(12) United States Patent
Flach

(10) Patent No.: US 9,161,859 B2
(45) Date of Patent: Oct. 20, 2015

(54) MULTILAYER WOUND DRESSING WITH CONDUCTIVE REGIONS

(75) Inventor: Niclas Flach, Alingsås (SE)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 283 days.

(21) Appl. No.: 13/809,555

(22) PCT Filed: Jul. 5, 2011

(86) PCT No.: PCT/SE2011/050908
§ 371 (c)(1),
(2), (4) Date: Mar. 28, 2013

(87) PCT Pub. No.: WO2012/008903
PCT Pub. Date: Jan. 19, 2012

(65) Prior Publication Data
US 2013/0178812 A1    Jul. 11, 2013

Related U.S. Application Data

(60) Provisional application No. 61/363,295, filed on Jul. 12, 2010.

(30) Foreign Application Priority Data

Jul. 12, 2010  (SE) ...................................... 1050781

(51) Int. Cl.
*A61F 13/15* (2006.01)
*A61F 13/00* (2006.01)
(Continued)

(52) U.S. Cl.
CPC ......... *A61F 13/0206* (2013.01); *A61F 13/0203* (2013.01); *A61N 1/0456* (2013.01);
(Continued)

(58) Field of Classification Search
CPC .................. A61F 13/0206; A61F 2013/00089; A61F 2013/0034; A61N 2001/34; A61N 2001/327; A61N 2001/326
USPC ..................... 604/367, 361, 362, 304; 602/48
See application file for complete search history.

(56) References Cited

U.S. PATENT DOCUMENTS 3,658,726 A * 4/1972 Mühl ........................ 252/519.3
4,067,342 A    1/1978 Burton et al.
(Continued)

FOREIGN PATENT DOCUMENTS

CN    1206352 A    1/1999
EP    0367320       5/1990
(Continued)

OTHER PUBLICATIONS

International Preliminary Report on Patentability issued Jan. 15, 2013 for International Patent Application No. PCT/SE2011/050908, which was filed on Jul. 5, 2011, and which was published as WO 2012/008903 on Jan. 19, 2012 (Inventor—Flach; Applicant—Molnlycke Health Care AB) (pp. 1-7).
(Continued)

*Primary Examiner* — Jacqueline Stephens
(74) *Attorney, Agent, or Firm* — Ballard Spahr LLP

(57) ABSTRACT

Provided is a wound dressing including a wound pad of absorbent material having a first side and a second side opposite thereto, a backing layer covering the wound pad on the first side thereof an adhesive layer for attaching the dressing to skin. The backing layer has at least one conductive region and consists of plastic film.

12 Claims, 1 Drawing Sheet

(51) Int. Cl.
*A61F 13/02* (2006.01)
*A61N 1/04* (2006.01)
*A61N 1/36* (2006.01)

(52) U.S. Cl.
CPC .......... *A61N1/0468* (2013.01); *A61N 1/36014* (2013.01); *A61F 2013/0034* (2013.01); *A61F 2013/00089* (2013.01)

(56) References Cited

U.S. PATENT DOCUMENTS

| | | | |
|---|---|---|---|
| 4,398,454 A * | 8/1983 | Lambros et al. | 99/285 |
| 4,779,630 A | 10/1988 | Scharnberg et al. | |
| 5,470,625 A * | 11/1995 | Perrault | 428/48 |
| 5,833,716 A | 11/1998 | Bar-Or | 607/153 |
| 5,844,013 A * | 12/1998 | Kenndoff et al. | 521/137 |
| 5,974,344 A | 10/1999 | Shoemaker | 607/149 |
| 6,263,226 B1 | 7/2001 | Axelgaard et al. | |
| 7,043,308 B2 * | 5/2006 | Cohen | 607/152 |
| 7,689,285 B2 | 3/2010 | Garabet | 607/50 |
| 2004/0162602 A1 | 8/2004 | Cohen | 607/152 |
| 2006/0003133 A1 | 1/2006 | Johnson | 428/40.1 |
| 2007/0203442 A1 | 8/2007 | Bechert | 602/48 |
| 2010/0217177 A1 * | 8/2010 | Cali et al. | 604/23 |

FOREIGN PATENT DOCUMENTS

| | | |
|---|---|---|
| EP | 0504715 | 9/1992 |
| EP | 1589918 | 8/2010 |
| GB | 1556364 A | 11/1979 |
| WO | WO 99/15101 | 4/1999 |
| WO | WO 02/089911 | 11/2002 |
| WO | WO 03/090654 | 11/2003 |
| WO | WO 2008/071941 | 6/2008 |

OTHER PUBLICATIONS

International Search Report and Written Opinion issued Oct. 28, 2011 for International Patent Application No. PCT/SE2011/050908, which was filed on Jul. 5, 2011, and which was published as WO 2012/008903 on Jan. 19, 2012 (Inventor—Flach; Applicant—Molnlycke Health Care AB) (pp. 1-12).

* cited by examiner

MULTILAYER WOUND DRESSING WITH CONDUCTIVE REGIONS

CROSS-REFERENCE TO RELATED APPLICATIONS

The present application is a U.S. National Phase Application of International Application No. PCT/SE2011/050908, filed Jul. 5, 2011, which claims priority to Swedish Patent Application No. 1050781-2, filed Jul. 12, 2010, and U.S. Patent Application No. 61/363,295, filed Jul. 12, 2010, all of which applications are incorporated herein fully by this reference.

TECHNICAL FIELD

The present invention relates to a wound dressing including a wound pad of absorbent material having a first side and a second side opposite thereto, a backing layer covering the wound pad on the first side thereof and an adhesive layer for attaching the dressing to skin.

BACKGROUND OF THE INVENTION

Electric stimulation has been proven to promote wound healing and many appliances for performing electrical stimulation to a wound are known in prior art. In many appliances, conductive wires or the like leading from a conductive sheet passes trough a backing layer of the appliance. For such appliances, it is hard to obtain liquid tightness in the backing layer in openings through which a wire passes. In other appliances, such as EP 1 589 918 and EP 0 504 715, an electrical contact projects from an opening in the backing layer of the appliance. In both cases, an outer barrier for protecting against external bacteria or the like and preventing exudates from leaking through the backing layer can not be warranted.

WO 02/089911 A1 discloses a two part TENS (Transcutaneous Electrical Nerve Stimulator) device having a lower part having a top layer made of a magnetic polymer and conductive adhesive forming electrodes in contact with the skin. Two conductive pads extend through the top layer of the lower part and connect to the conductive adhesive and to electrical contacts in the upper part of the device which contains an electronic module for controlling the electrical stimulation.

Electrical stimulation treatment of wounds is intermittently performed and it would be a great advantage if an appliance for electrical stimulation of wounds can function as a conventional wound dressing during periods between the treatments by electrical stimulation, thereby eliminating the necessity of removing (probably changing) wound dressings after every treatment period of electrical stimulation. Furthermore, several types of TENS devices are known and used for relieving pain in a variety of ways. It would be an advantage if the electrodes of such devices could be attached to a contact on a dressing for enabling electrical stimulation of a wound.

The objective of the invention is to improve a wound dressing enabling electrical stimulation of the wound so that it can function also as a conventional wound dressing and enables easy attachment of TENS electrodes for the electrical stimulation.

SUMMARY OF INVENTION

This objective is accomplished by a wound dressing including a wound pad of absorbent material having a first side and a second side opposite thereto, a backing layer covering the wound pad on the first side thereof and an adhesive layer for attaching the dressing to skin, characterized in that the backing layer has at least one conductive region and consists of plastic film. By providing the at least one conductive region on the backing layer, the electrode of existing TENS devices can be directly attached to this region without the need for intermediate contact components.

In a preferred embodiment, the backing layer extends beyond the wound pad along its periphery and the adhesive layer is attached to the backing layer on the side thereof proximate to the wound pad at least in the peripheral area thereof extending beyond the wound pad. Since the backing layer is intact in such a dressing, the barrier against external contamination by for example bacteria is intact. A wound dressing according to the present invention can thus be used as a conventional wound dressing when it is desired not use electrical stimulation or during periods between such stimulation.

In a first preferred embodiment the backing layer can have only one conductive region or alternatively the backing layer can have two or more conductive regions. If the wound dressing has more than one conductive region, both the anode and the cathode of a TENS device or other device for electrical stimulation can be attached to the backing layer.

In a second preferred embodiment the backing layer as a whole consists of a conductive plastic film.

The at least one conductive region of the backing layer is preferably a piece of conductive plastic film affixed to the edge of an opening in the non-conductive part of the backing layer.

The non-conductive part of the backing layer consists preferably of polyurethane and the at least one conductive region of the backing layer consists preferably of polyurethane filled with carbonaceous substance, preferably carbon black.

In a third preferred embodiment a conductive liquid permeable sheet extends over at least a part of the second side of the wound pad to at least one of two opposite edges of said second side, from said at least one of two opposite edges to the first side of the wound pad, said conductive sheet being conductively connected to a conductive region of the backing layer. Preferably, the conductive sheet covers the whole distance between said two opposite edges and is conductively connected to a conductive region of the backing layer at two opposite regions on the first side of the wound pad. This is of course necessary in case the anode and the cathode of the electrical stimulation device are attached to separate conductive regions of the backing layer. The liquid permeability of the conductive liquid permeable sheet is preferably obtained by the sheet being perforated at least in the part thereof extending over the second side of the wound pad.

The wound pad can consist of absorbent foam but other absorbent materials known to be used in wound pads can also be used.

BRIEF DESCRIPTION OF THE DRAWING

The invention will now be described with reference to the enclosed figures, of which.

DESCRIPTION OF EMBODIMENTS

Figure 1:
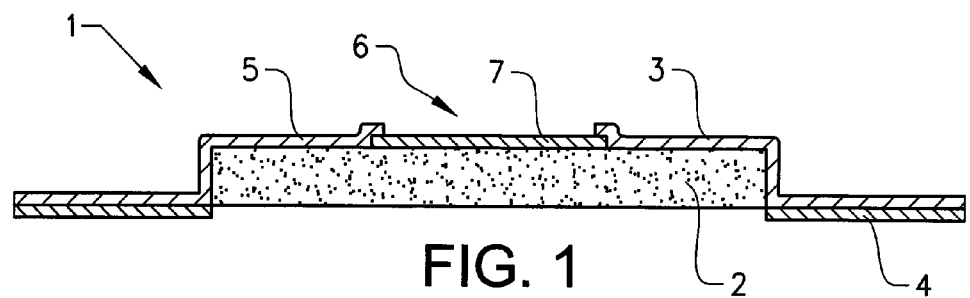
FIG. 1 schematically discloses a sectional view of a wound dressing according to a first preferred embodiment of the invention, FIG. 2 discloses in a view similar to FIG. 1, a wound dressing according to a second preferred embodiment of the invention, FIG. 3 discloses in a view similar to FIG. 1, a wound dressing according to a third preferred embodiment, and FIG. 4 discloses in a view similar to FIG. 1 a wound dressing according to a fourth preferred embodiment.

In FIG. 1, a first preferred embodiment of a wound dressing 1 is schematically shown in a sectional view. The wound dressing 1 comprises a wound pad 2 of absorbent material which on its outside is covered by a backing layer 3 which extends beyond the circumference of the wound pad 2. The backing layer 3 is on its inside coated with an adhesive 4 at least on the region thereof extending beyond the circumference of the wound pad.

The term "outside" refers to a side of a component in the wound dressing distal from the skin when the wound dressing is applied over a wound and the term "inside" refers to a side proximal to the skin.

The backing layer 3 is composed of a first plastic film 5 having a hole 6 therein and a second plastic film 7 affixed to the first plastic film along the edge of the hole 6. According to the present invention the second plastic film 7 is a conductive plastic film. By the term "conductive plastic film" is meant a plastic material which during its manufacture is filled with conductive fillings, such as carbon black. Such a plastic film is conductive through its thickness and not only on a surface thereof. In this respect it is pointed out that the electrical stimulation to be performed involves the application of current pulses to the wound. The plastic material thereby need not be filled with conductive fillings to such a degree that direct current can flow through the conductive film, it is sufficient that the plastic material is filled to such a degree that a "capacitive" conductivity is obtained, i.e. that the conductive fillings in the plastic material can attract electrons in the same way as the electrodes in a capacitor. However, it is preferred that the plastic material is filled to such a degree that direct current can flow in the conductive plastic film produced. The conductive plastic film 7 is preferably affixed to the inside of the first plastic film 5.

After applying wound dressing 1 over a wound, an electrode of a conventional TENS device can be attached to the outside of the conductive film 7 in the same way as such an electrode is attached to skin during conventional use thereof. An electric stimulation of the wound can now occur providing that the wound pad has been conductive by the absorption of wound exudates. If a wound is only slightly excuding the wound pad or a part thereof can be filled with hydrogel or any other gel-like conductive material before the application of the wound pad in order to enable electrical stimulation of the wound bed. This could also be done for moderate or highly excuding wounds if it is desired to perform electrical stimulation of the wound directly after application of the wound dressing.

When the electric stimulation of the wound has been performed, the electrode is removed from the conductive plastic film 7 and the wound dressing 1 will now function as a conventional wound dressing.

In a variant more than one hole is made in plastic film 5, each hole being covered by a conductive plastic film, in order to enable the attachment of more than one electrode to wound dressing 1. Thereby, both an anode and a cathode can be applied to the backing layer.

Figure 2:
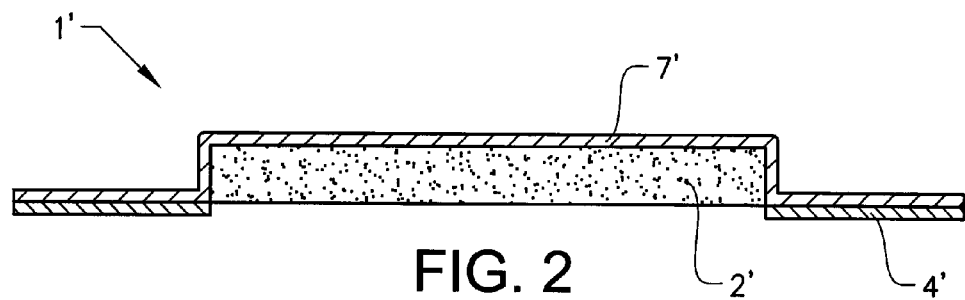

In FIG. 2, a wound dressing 1' according to second preferred embodiment is schematically shown. This wound dressing 1' differs from the wound dressing 1 shown in FIG. 1 only in that the backing layer as a whole is constituted by a conductive plastic film 7'. Components of the wound dressing 1' corresponding to similar components in the wound dressing 1 in FIG. 1 are given the same reference numerals with the addition of a prime sign. To such a wound dressing only anode(s) or cathode(s) can be attached.

Figure 3:
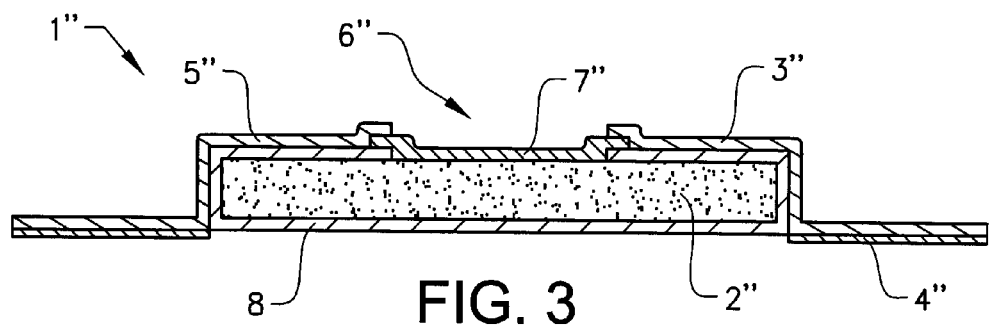

In FIG. 3, a third preferred embodiment of a wound dressing 1" according to the invention is schematically shown. Components of the wound dressing 1" corresponding to similar components in the wound dressing 1 in FIG. 1 are given the same reference numerals with the addition of a bis sign. The wound dressing 1" according to the third embodiment differs from the wound dressing 1 according to the first embodiment shown in FIG. 1 in that a conductive sheet 8 is extending over at least a part of the inside of absorbent pad 2", over at least a part of opposite sides thereof, and in over the outside of the absorbent pad 2" and in under the edges of the conductive plastic film 7". In the region where the conductive film 7" and the conductive sheet 8 overlap each other, they are in contact with each other, preferably affixed to each other, for example by a weld seam or an adhesive connection.

The conductive sheet 8 can be a conductive plastic film like the plastic film 7" but can also be a plastic film coated with a conductive coating, a laminate of a plastic film and a metallic sheet or a metallic sheet. It is also possible to make conductive patterns on the surface of a plastic film with the aid of conductive ink. In this respect it is pointed out that a conductive surface of the conductive sheet 8 should be present on the side of sheet 8 turned against the wound when wound dressing 1" is applied to a wound.

The conductive sheet 8 is also perforated, at least on the side thereof covering the inside of the wound pad 2" or a part thereof, in order to allow the wound pad to absorb exudates also in the area covered by the conductive sheet 8.

The advantage with the wound dressing 1" in comparison with the wound dressings 1 and 1' according to the first and second embodiment is that with the wound dressing 1" the electric stimulation of an excuding wound can start immediately after application of the wound dressing 1" and is not dependent on wetting of the wound pad by exudates, hydrogel or the like.

In FIG. 3, the backing layer 3" is a backing layer similar to the backing layer 3 shown in FIG. 1. Also in the third embodiment illustrated in FIG. 3 more than one hole can be made in the non conductive plastic film 5" and be covered by conductive plastic films as is described for the wound dressing 1 shown in figure. It is also possible to instead of backing layer 3" shown in FIG. 3 provide a backing layer which as a whole is made of conductive plastic film as in the second embodiment shown in FIG. 2.

The plastic material in the backing layer 3,7', 3" is preferably polyurethane but other plastic materials, such as polyester, polyethylene, can also be used. It is preferred that the same plastic material is used for the non conductive plastic film of the backing layer as well as for the conductive plastic film but this is not necessary.

The filler in the conductive plastic film is preferably carbon black but other carbonaceous substances can be used such as carbon fibres and carbon nanotubes. It is also possible to use other conductive fillers such as silver-coated glass, nickel-coated graphite or metal fillers.

The wound pad 2,2',2" is preferably made of absorbent foam, for example polyurethane foam, but all other materials known to be used in absorptive wound pads can be used.

The adhesive in the adhesive layer 4, 4', 4" is preferably a silicone gel adhesive but other adhesives known to be used in wound dressings, such as acrylate adhesives, can also be used.

Figure 4:
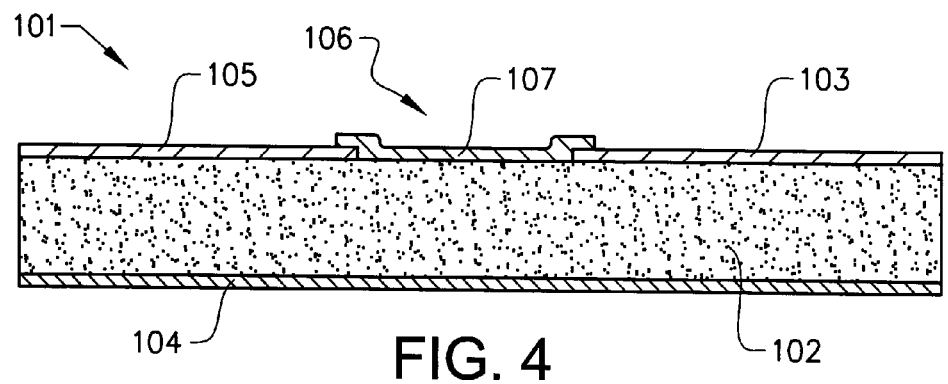

The inventive concept of providing a dressing having an attachment area at which an electrode can be easily attached can of course also be used for dressings in which an outer barrier for protecting against bacteria or the like and preventing exudates from leaking out of the dressing is not necessary. In FIG. 4 a dressing 101 is schematically disclosed in which the backing layer 103 only covers the outside of the wound pad 102 and does not extend beyond the periphery thereof. The wound pad 102 consists preferably of absorbent foam. The dressing 101 is releasably attached to skin by an adhesive layer 104. According to the invention the backing layer 103 is comprised of a non-conductive plastic film 105 and a conductive plastic film 107 which cover an opening 106 in the film 105 and is affixed to film 105 around the edges of opening 106. Backing layer 103 can be provided with more than one conductive part and/or a conductive sheet like the sheet 8 in FIG. 3 can be provided.

Before use, the wound dressing is as is usual in the art provided with a release layer protecting the adhesive layer from dirt and contaminations and also from drying out.

The disclosed embodiments can be modified without leaving the scope of the invention. An adhesive layer can for example be extended over the inside of the wound pad. Such an adhesive layer should be liquid permeable, e.g. perforated, in order to allow the wound pad to absorb exudates from the wound and can carried by a perforated carrier, for example of plastic material. The wound pad can consist of more than one layer and can contain super absorbent particles or the like. Furthermore, the conductive liquid permeable sheet in the third embodiment can be made of liquid permeable fabric or nonwoven instead of a perforated sheet. The invention should therefore only be limited of the content of the enclosed patent claims.

The invention claimed is:

1. A wound dressing comprising:
   a wound pad of absorbent material having a first side and a second side opposite to the first side, wherein the second side of the wound pad of absorbent material is arranged to contact a wound during use of the wound dressing;
   a backing layer covering the wound pad on the first side thereof; and
   an adhesive layer for attaching the dressing to skin,
   wherein the backing layer has at least one conductive region and comprises plastic film, wherein the at least one conductive region is conductively connected to at least a portion of the first side of the wound pad of absorbent material, wherein the backing layer extends beyond the wound pad along its periphery and the adhesive layer is attached to the backing layer on the side thereof proximate to the wound pad at least in the peripheral area thereof extending beyond the wound pad.

2. The wound dressing according to claim 1, wherein the backing layer has two or more conductive regions.

3. The wound dressing according to claim 1, wherein the at least one conductive region comprises a conductive plastic film.

4. The wound dressing according to claim 1, wherein the at least one conductive region of the backing layer is a piece of conductive plastic film affixed to the edge of an opening in a non-conductive part of the backing layer.

5. The wound dressing according to claim 1, wherein a non-conductive part of the backing layer comprises polyurethane.

6. The wound dressing according to claim 1, wherein the at least one conductive region of the backing layer comprises polyurethane filled with carbonaceous substance.

7. The wound dressing according to claim 6, wherein the carbonaceous substance comprises carbon black.

8. The wound dressing according to claim 1, wherein a conductive liquid permeable sheet extends over at least a part of the second side of the wound pad to cover at least one of two opposite edges of said second side, from said at least one of two opposite edges to the first side of the wound pad, said conductive sheet being conductively connected to the backing layer.

9. The wound dressing according to claim 8, wherein the conductive liquid permeable sheet is perforated at least in the part thereof extending over the second side of the wound pad.

10. The wound dressing according to claim 1, wherein the wound pad comprises absorbent foam.

11. The wound dressing according to claim 1, wherein the at least one conductive region is in contact with at least a portion the first side of the wound pad of absorbent material.

12. The wound dressing according to claim 1, wherein the wound pad of absorbent material comprises a conductive material.

* * * * *